United States Patent
Nishiyori et al.

(10) Patent No.: US 8,476,898 B2
(45) Date of Patent: Jul. 2, 2013

(54) ROPE TESTER DETECTION PLATE

(75) Inventors: Koichiro Nishiyori, Tokyo (JP); Hiroshi Sasai, Tokyo (JP); Takashi Yoshioka, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 232 days.

(21) Appl. No.: 12/742,648

(22) PCT Filed: Nov. 13, 2007

(86) PCT No.: PCT/JP2007/071995
§ 371 (c)(1), (2), (4) Date: May 12, 2010

(87) PCT Pub. No.: WO2009/063549
PCT Pub. Date: May 22, 2009

(65) Prior Publication Data
US 2010/0259253 A1    Oct. 14, 2010

(51) Int. Cl.
 *G01N 27/82* (2006.01)
 *B66B 3/00* (2006.01)
(52) U.S. Cl.
 USPC .......................... 324/240; 324/238; 187/393
(58) Field of Classification Search
 USPC .................... 324/240, 238; 187/393
 See application file for complete search history.

(56) References Cited

U.S. PATENT DOCUMENTS

| | | | | |
|---|---|---|---|---|
| 4,096,437 A | * | 6/1978 | Kitzinger et al. | 324/227 |
| 4,145,920 A | | 3/1979 | Yamagami | |
| 4,427,940 A | * | 1/1984 | Hirama et al. | 324/240 |
| 2003/0111143 A1 | * | 6/2003 | Wheeler, Jr. | 148/587 |
| 2007/0090834 A1 | * | 4/2007 | Osada et al. | 324/240 |

FOREIGN PATENT DOCUMENTS

| | | |
|---|---|---|
| EP | 1 676 806 A1 | 7/2006 |
| EP | 1 914 186 A1 | 4/2008 |
| JP | 53-013752 A | 2/1978 |
| JP | 9-290973 A | 11/1997 |
| JP | 2001-063938 A | 3/2001 |

OTHER PUBLICATIONS

International Search Report of Application PCT/JP2007/071995 dated Aug. 12, 2008.

* cited by examiner

*Primary Examiner* — Patrick Assouad
*Assistant Examiner* — David M. Schindler
(74) *Attorney, Agent, or Firm* — Buchanan Ingersoll & Rooney PC

(57) ABSTRACT

In order to examine abnormality in shape of an outer circumference of a wire rope, the rope tester device includes a comb-shaped detection plate having a curved test edge portion extending along at least one portion of an outer circumference of a substantially circular sectional configuration of the wire rope and a testing recessed portion for receiving the wire rope in the vicinity of or in contact with the test edge portion, and a support device for rotatably supporting the detection plate in the vicinity of or in contact with the wire rope for permitting the rotation of the detection plate when the detection plate receives a force from an abnormal portion of the wire rope to relieve the force. A test string is disposed in an opening of the testing recessed portion for testing a surface that is not in the vicinity of or in contact with the test edge portion.

10 Claims, 5 Drawing Sheets

ROPE TESTER DETECTION PLATE

TECHNICAL FIELD

This invention relates to a rope tester device for easily detecting an abnormality of an elevator rope.

BACKGROUND ART

In the conventional rope tester device, detection of an abnormality such as the rope strand breakage, strand breakage, diameter expansion, foreign matter deposit, etc. is achieved by holding by hand a tester of a frame structure with a wire close to the rope, bringing the wire in contact with the running rope while the elevator is being driven and by sensing the vibration of the wire by hand of the personnel (see Patent Document 1, for example).

[Patent Document] Japanese Patent Laid-Open No. 2001-63938

DISCLOSURE OF THE INVENTION

Problem to be Solved by the Invention

In such the test device, the wire is in contact with only one portion of the rope, so that the only one portion of the outer circumference of the rope can be tested, and the remaining rope surface is left un-tested. Also, since the tester device is held by hand of a personnel, the running speed of the elevator is suppressed for the safety reason, resulting in an elongated period of the test.

Accordingly, the object of the present invention is to provide a rope tester device that can test most portion of the rope surface.

Measure for Solving the Problem

The rope tester device of the present invention comprises a detection plate having a curved test edge portion extending along at least one portion of an outer circumference of a sectional configuration of a wire rope and a recessed portion for receiving the wire ropes in the vicinity of or in contact with the test edge portion.

Advantageous Result of the Invention

According to the present invention, the detection plate hits a radially projecting substance of the rope at the detection edge portion curved along the outer circumference of the rope so that an abnormality in a wide region of the rope surface can be detected.

BRIEF DESCRIPTION OF THE DRAWINGS

FIG. 8 is a detailed perspective view as viewed from the rope side of the rope tester device shown in FIG. 1; (Embodiment 1)

BEST MODE FOR CARRYING OUT THE INVENTION

The best mode for carrying out the present invention will now be described.

[Embodiment 1]

Figure 1:
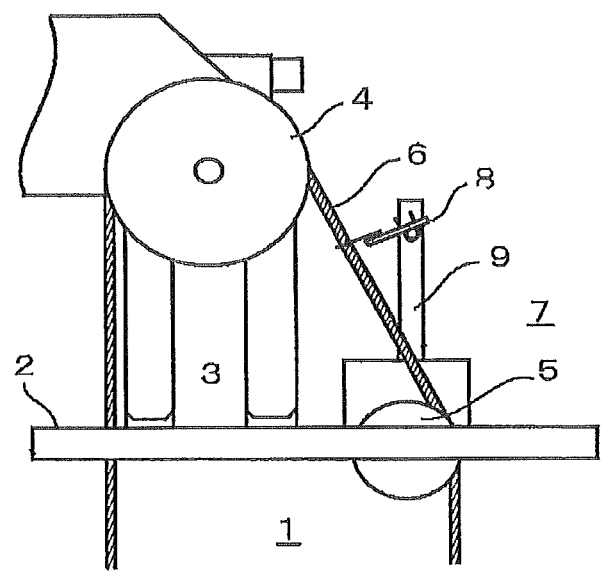
FIG. 1 is a schematic side view showing the rope tester device of Embodiment 1 of the present invention; (Embodiment 1)
Figure 2:
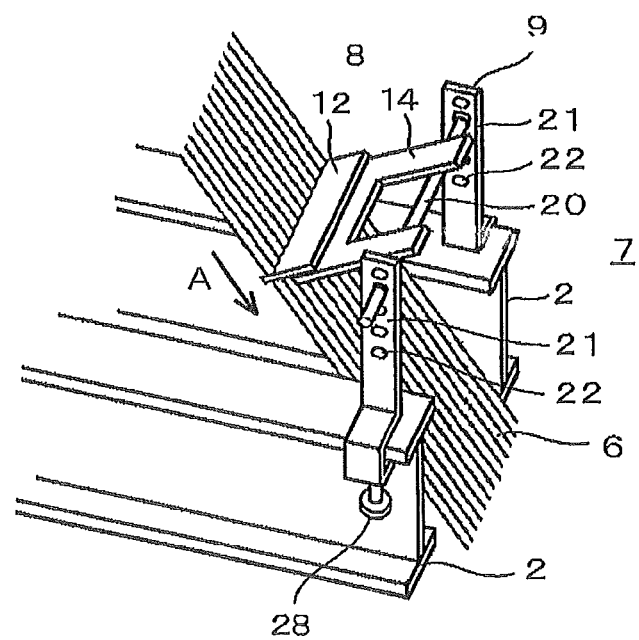
FIG. 2 is a perspective view showing the rope tester device of FIG. 1; (Embodiment 1)
Figure 3:
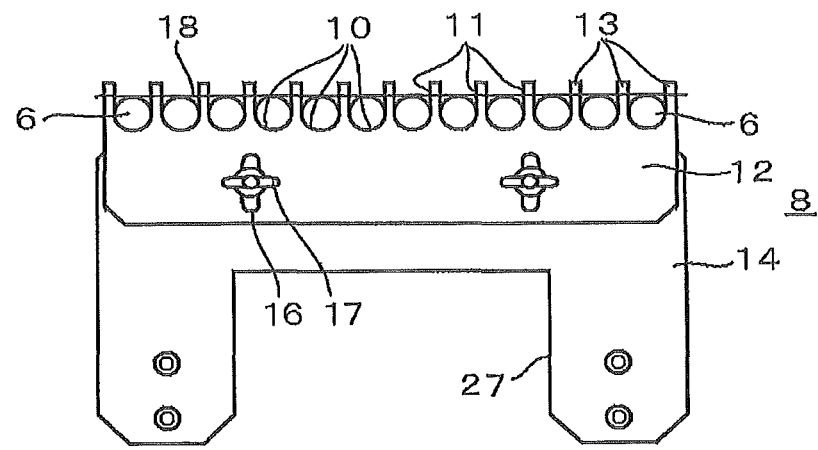
FIG. 3 is a plan view showing the detection plate; (Embodiment 1)
Figure 4:
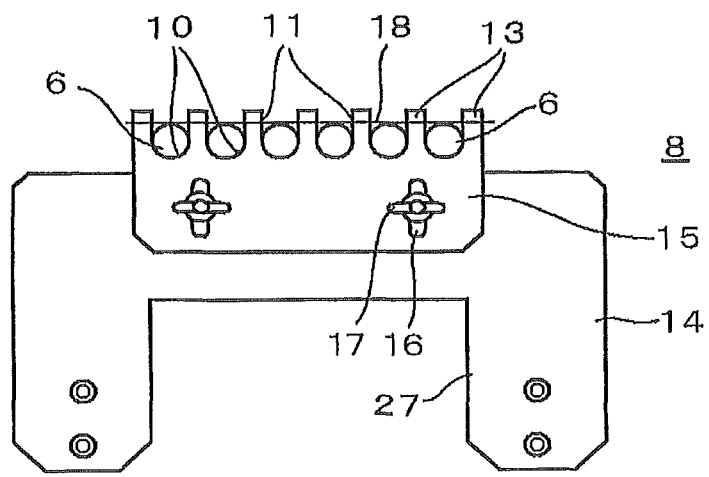
FIG. 4 is a plan view showing another example of the detection plate; (Embodiment 1)
Figure 5:
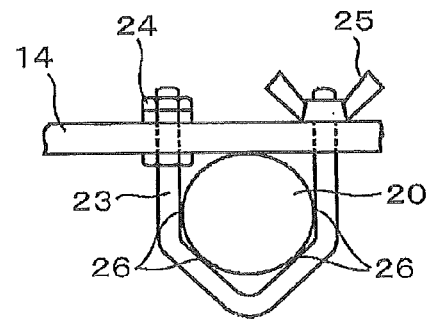
FIG. 5 is a view showing the connection portion between the detection plate and the mounting shaft; (Embodiment 1)
Figure 6:
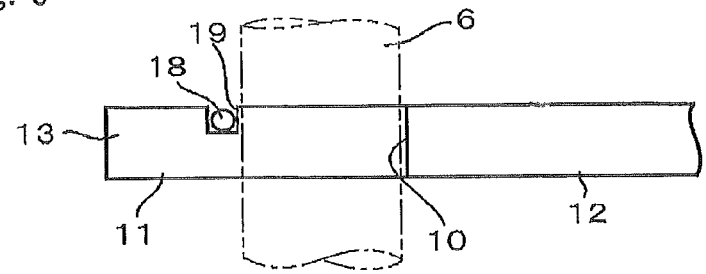
FIG. 6 is a sectional view showing the detection string of the detection plate; (Embodiment 1)
Figure 7:
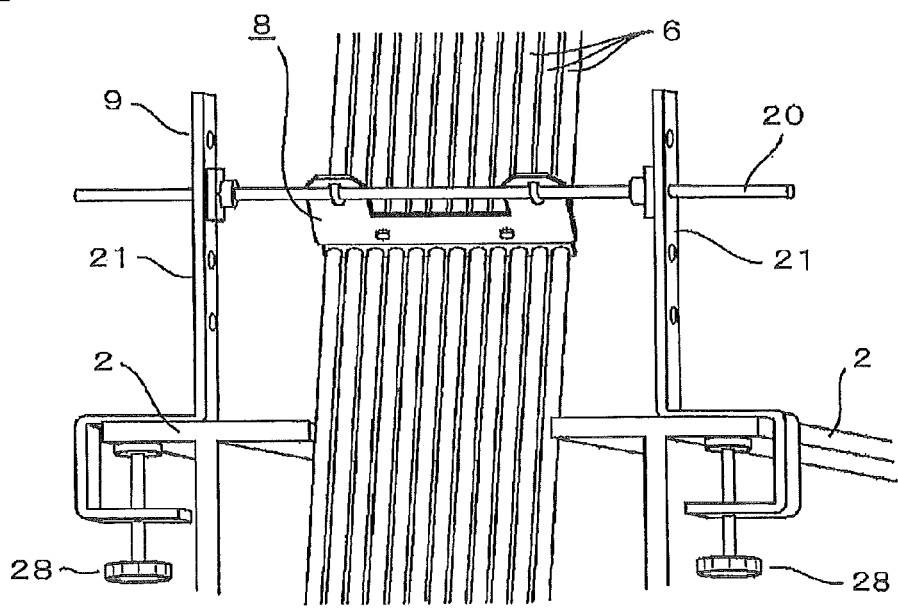
FIG. 7 is a detailed perspective view as viewed from the bottom of the detection plate of the rope tester device shown in FIG. 1; (Embodiment 1)
Figure 9:
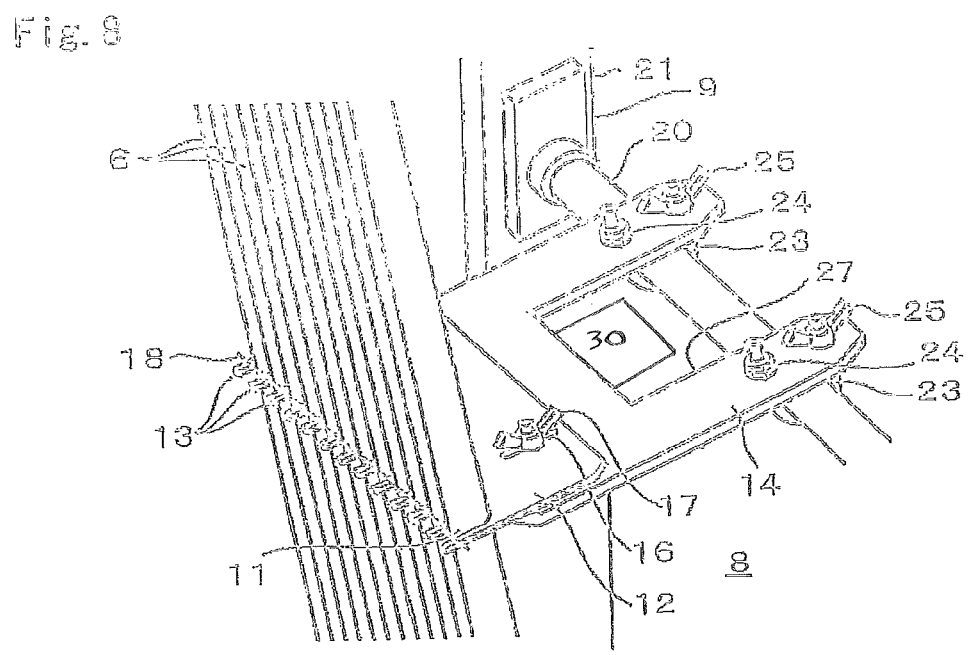
FIG. 9 is a detailed perspective view of the rope tester showing the notched portion.
Figure 9:
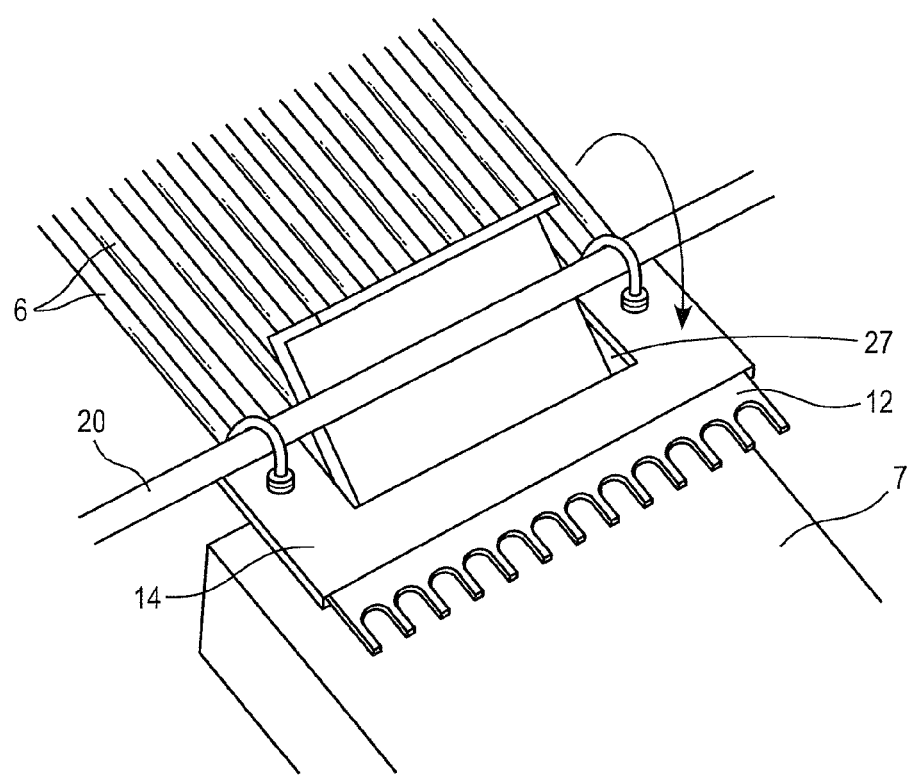

FIGS. 1-8 are views showing the rope tester device of Embodiment 1 of the present invention. FIG. 1 is a schematic side view showing the rope tester device used in abnormality detection of the wire ropes of an elevator system, FIG. 2 is a perspective view of the rope tester device, FIG. 3 is a plan view showing one example of the detection plate, and FIG. 4 is a plan view showing another example of the detection plate. FIG. 5 is a view showing the connection portion between the detection plate and the mounting shaft, and FIG. 6 is a sectional view showing the detection string of the detection plate. Also, FIG. 7 is a detailed perspective view as viewed from the bottom of the detection plate of the rope tester device and FIG. 8 is a detailed perspective view as viewed from the rope side of the rope tester device.

In FIG. 1, a hoistway 1 of an elevator has provided at its top portion with a machine bed 2 on which a machine room 3 is defined. Within the machine room 3, a hoist 4 and a deflector sheave 5 are disposed, around which wire ropes 6 for moving an elevator car are wound. A rope tester device 7 of the present invention is disposed at a position closed to the wire ropes 6 extended between the hoist 4 and the deflector sheave 5 on the machine bed 2.

The rope tester device 7 comprises a detection plate 8 disposed in the vicinity of or in contact with the an outer circumferential surface of the running wire ropes 6 to detect an abnormality of the surface of the wire ropes 6, and a support device 9 for supporting the detection plate 8 in the test position in the vicinity of the wire ropes 6 at the test position.

As best shown in FIG. 3, the detection plate 8 has a curved test edge portion 10 extending along at least one portion of an outer circumference of a substantially circular cross-sectional configuration of the wire ropes 6, and a recessed portion 11 for receiving the wire ropes 6 in the vicinity of or in contact with the test edge portion 10. In the illustrated example, the recessed portion 11 of the test edge portion 10 extends along about ½ of the outer circumference of the circular cross-sectional configuration of the wire ropes 6.

The detection plate 8 has provided with a comb-shaped member 12 having a number of the recessed portion 11 in correspondence with the number of the wire ropes 6 to be tested, this being desirable in that the plurality of wire ropes 6 can be simultaneously tested at a single pass of the wire ropes 6. In the illustrated example shown in FIG. 3, twelve wire ropes 6 are used, so that the comb-shaped member 12 has twelve recessed portions 11 and thirteen parallel tooth portions 13 defining the recessed portion therebetween.

The number of the recessed portion 11 of the detection plate 8 is desirable when it corresponds to the number of the wire ropes 6 to be detected, but the detection plate 8 with a plurality of the recessed portion 11 may be used for a single wire rope 6. The configuration of the curved portion of the recessed portion 11 of the detection plate 8 is desirable when it is circular, it may be a polygonal as long as the detection edge portion 10 in the vicinity of or in contact with the outer circumference of the wire ropes 6 and extending in the circumferential direction can be provided.

The detection plate 8, which may be constructed as a single plate-shaped member, comprises in the illustrated example the comb-shaped member 12 in which the recessed portion 11 is formed and a base 14 for holding the comb-shaped member 12 as an separate part and connectable to the support device 9 which will be described in detail later. With such the structure, when the rope tester is to be used in an elevator having a different pitch or the number of ropes, the tester can be used by changing the comb-shaped member 12 only. When there are twelve wire ropes 6 as illustrated, the detection plate 8 shown in FIG. 3 can be used, and when there are six wire ropes 6, a comb-shaped member 15 having six recessed portion 11 and seven teeth portion 13 as shown in FIG. 4 can be used. Also, the comb-shaped portion in the vicinity of or in contact with the projection portion of the rope, which is a wearable portion, can be minimized.

The comb-shaped member 12 is detachably and position adjustably held on the base 14 by a fastening means such as an elongated hole 16 and a wing screw 17 so that the comb-shaped member 12 can be easily replaced and the comb-shaped member 12 can be easily position adjusted with respect to the base 14 by loosening the wing screw 17 and moving the comb-shaped member 12 along the elongated hole 16. Such the fastening means may be replaced by a small screw, a clip, a toggle clamp or the like.

In FIG. 6, the detection plate 8 also comprises a test string 18 provided close to the tip of the teeth portion 13 of the comb-shaped portion 13 so as to close the recessed portion 11, the comb-shaped portion 12 being in the vicinity of or in contact with an outer circumference other than the outer circumference in the vicinity of or in contact with the test edge portion 10 with respect to the wire ropes 6 received in the recessed portion 11. The test string 18 is disposed in grooves 19 provided at teeth portions 13 defining an opening of the recessed portion 11 of the comb-shaped member 12.

The test string 18 is in the vicinity of or in contact with the outer circumferential surface on the side of the outer circumferential surface of the wire ropes 6 that cannot be tested by the test edge portions 10 of the comb-shaped member 12, so that the test can be carried out in terms of that portion. The grooves 19 disposed in the teeth portions 13 position the test string 18 at a predetermined position and hold it not to be displaced from the predetermined position even when its is brought into contact with the wire ropes 6. The test string 18 is made of a material that can be broken or raveled upon the contact with the projection or an abnormal portion of the wire ropes 6, thus enabling the abnormality of the surface of the wire ropes 6 to be detected.

When the position of the grooves 19 is changed so that the test string 18 is secured on the teeth portion 19 at a position on the right hand of the position shown in FIG. 6, then the test string 18 is brought into line contact with the outer circumferential surface of the wire ropes 6, enabling the test of the outer circumferential surface to be carried out over a wider range.

The support device 9 supporting the detection plate 8 at the test position in relation to the wire ropes 6 is arranged such that its comb-shaped member 12 rotatably supports the detection plate 8 in the vicinity of or in contact with the wire ropes 6 and permits the rotation of the detection plate 8 when the detection plate 8 receives a force from an abnormal portion projecting from the surface of the wire ropes 6 to relieve the force from the wire ropes 6.

The support device 9 of the rope tester device 7 also comprises, as best shown in FIGS. 2, 7 and 8, a mounting shaft 20 disposed at said test position and extending perpendicular to the running direction of the wire ropes 6 as shown in an arrow A in FIG. 2 and parallel to the direction of arrangement of the plurality of wire ropes 6.

The mounting shaft 20, which in the illustrated example is a cylindrical shaft member supported by two support pillars 21 mounted to the machine bed 2, is supported by being selectively inserted into a plurality of mounting holes 22 disposed in the support pillars 21 so that the level of the support pillars 21 themselves can be adjusted. While the support pillars 21 are detachably fixed to the machine bed 2 by a vice-shaped clamp mechanism 28 as best shown in FIG. 7, a magnetic attractive force and a vacuum suction force other than mechanical fastening or their combination can be equally utilized.

The support device 9 of the rope tester device 7 also comprises a U-bolt 23 which is a clamp extending across over the mounting shaft 20 and connected to the base 14 of the detection plate 8 as shown in FIG. 5. The U-bolt 23 has both end portions extending through the base 14 and secured by the nut 24 and the wing screw 25, the extent of the securing between the mounting shaft 20 and the detection plate 8 can be determined by the tightening of the wind screw 25. The U-bolt 23 may have a typical U or J-shape configuration in which the bight portion is circular, or may be a polygonal bolt having a bight portion bent into a polygonal shape.

The illustrated U-bolt 23 is a polygonal bolt having a bight portion bent into a polygonal shape, making a frictional contact at very small contact portions 26 which can be said to be point contacts between the U-bolt 23 and the mounting shaft 20, so that the tightening force of the wing screw 25 is easily transmitted to the mounting shaft 20, making the tightening easy and securing force proper.

Thus the detection plate 8 can be easily positioned with respect to the wire ropes 6 by the position adjusting means such as the elongated hole 16 and the wing screw 17 between the comb-shaped member 12 and the base 14, the rotation permitting means including the mounting shaft 20 and the U-bolt 23, as well as the level adjusting means including the plurality of mounting holes 22 formed in the support pillars 21.

That is, with the construction as above described, the comb-shaped member 12 and the base 14 are combined and connected to provide the detection plate 8 through the use of the elongated holes 16 so as to maximize the length dimension of the detection plate 8, the comb-shaped member 12 is brought into contact with the wire ropes 6 and the mounting shaft 20 is installed at a position where the detection plate 8 is rotatable about the mounting shaft 20. Then by loosening the wing screw 17 to decrease the connecting force between the comb-shaped member 12 and the base 14 and by sliding the comb-shaped member 12 toward the mounting shaft 20 by a length of the elongated holes 12, the clearances defined between the wire ropes 6 and the comb-shaped member 12 of the detection plate 8 can be easily maintained constant.

Also, by suitably selecting the length of the elongated holes 16 in the comb-shaped member 12, a fine adjustment of the position between the wire ropes 6 and the detection plate 8 can be made by the sliding displacement between the comb-shaped member 12 and the base 14.

Thus, the detection plate 8 is supported at the test position in relation to the wire ropes 6 so that the comb-shaped member 12 is supported in the vicinity of or in contact with the wire ropes 6, and the detection plate 8 is permitted to rotate when the comb-shaped member 12 receives a force from the wire ropes 6 to relieve the force.

The rope tester device 7 may be used in combination with a rope tester of the leakage magnetic flux measurement type, and for such case, the detection palate 8 of the rope tester device 7 of the present invention has a configuration that enables the positioning of the mounting position of the rope tester of the leakage magnetic flux measurement type, that is, the base 14 of the detection plate 8 is provided with a notched portion 27 for accommodating and positioning the rope tester therein. The use of this notched portion 27 makes the precise positioning and mounting of the rope tester of the leakage magnetic flux measurement type 30 with respect to the mounting shaft 20 after the test by the rope testing device 7 of the present invention has been finished.

Also, the dimensions of the detection plate 8 are determined such that, when a rope tester of the leakage magnetic flux measurement type for detecting the breakage of the wire ropes 6 is mounted to the mounting shaft 20 shown in FIG. 2, the distance between the tip portion of the comb-shaped member 12 of the detection plate 8 of the rope tester device 7 of the present invention is the same as the distance between the mounting shaft 20 and the wire ropes 6 when the rope tester is mounted to the same mounting shaft 20. The base 14 of the detection plate 8 is provided with the large notched portion 27 on the side of the mounting shaft 20 so that, when the rope tester is to be mounted on the mounting shaft 20 shown in FIG. 2, the rope tester can be mounted simply by flipping over the detection plate 8 about the mounting shaft 20 without detaching from the mounting shaft 20.

The embodiments heretofore described as the best mode for carrying out the invention are only for showing examples of the application of the present invention and not limiting the present invention. Also, the features of the various embodiments may be suitably combined and carried out.

The invention claimed is:

1. A rope tester device, comprising:
a detection plate including at least one recessed portion, each recessed portion having a curved test edge portion arranged to extend along at least one portion of an outer circumference of at least one wire rope and a plurality of teeth defining an opening of each recessed portion, each tooth including a groove; and
a test string provided to at least span the opening of the at least one recessed portion in a direction perpendicular to a longitudinal extension of the at least one wire rope, the test string being positioned by the grooves of the teeth.

2. The rope tester device as claimed in claim 1, comprising a support device for rotatably supporting said detection plate at a test position and for permitting rotation of said detection plate when said detection plate receives a force from an abnormal portion of the at least one wire rope to relieve said force.

3. The rope tester device as claimed in claim 1, wherein the at least one recessed portion includes a plurality of recessed portions, and said detection plate comprises a comb-shaped member in which the plurality recessed portions are provided in correspondence with a number of wire ropes to be tested.

4. The rope tester device as claimed in claim 2, wherein said detection plate comprises a comb-shaped member and a base connectable to said support device and for holding said comb-shaped member as a separate part.

5. The rope tester device as claimed in claim 4, wherein said comb-shaped member is adjustably held on said base.

6. The rope tester device as claimed in claim 4, comprising:
a leakage magnetic flux measurer.

7. The rope tester device as claimed in claim 6, wherein said base comprises a notch portion for receiving said leakage magnetic flux measurer.

8. The rope tester as claimed in claim 2, wherein said support device comprises a mounting shaft, extending at said test position, perpendicular to a running direction of the at least one wire rope and a U-bolt extending across over said mounting shaft and connected to said detection plate.

9. The rope tester device as claimed in claim 8, wherein said U-bolt has a plurality of linear sides.

10. The rope tester as claimed in claim 8, wherein said mounting shaft is adjustably supported.

* * * * *